United States Patent [19]

Mehra

[11] Patent Number: 4,832,718
[45] Date of Patent: * May 23, 1989

[54] PROCESSING NITROGEN-RICH, HYDROGEN-RICH, AND OLEFIN-RICH GASES WITH PHYSICAL SOLVENTS

[75] Inventor: Yuv R. Mehra, The Woodlands, Tex.

[73] Assignee: Advanced Extraction Technologies, Inc., Houston, Tex.

[*] Notice: The portion of the term of this patent subsequent to Nov. 18, 2003 has been disclaimed.

[21] Appl. No.: 100,242

[22] Filed: Sep. 23, 1987

Related U.S. Application Data

[63] Continuation-in-part of Ser. No. 74,226, Jul. 16, 1987, which is a continuation-in-part of Ser. No. 24,561, Mar. 11, 1987, which is a continuation-in-part of Ser. No. 854,383, Apr. 21, 1986, which is a continuation-in-part of Ser. No. 828,996, Feb. 13, 1986, Pat. No. 4,696,688, which is a continuation-in-part of Ser. No. 828,988, Feb. 13, 1986, Pat. No. 4,680,042, which is a continuation-in-part of Ser. No. 808,463, Dec. 13, 1985, Pat. No. 4,692,179, which is a continuation-in-part of Ser. No. 784,566, Oct. 4, 1985, Pat. No. 4,817,038, which is a continuation-in-part of Ser. No. 759,327, Jul. 26, 1985, Pat. No. 4,623,371, which is a continuation-in-part of Ser. No. 758,351, Jul. 24, 1985, Pat. No. 4,601,738, which is a continuation-in-part of Ser. No. 637,210, Aug. 3, 1984, Pat. No. 4,578,094, which is a continuation-in-part of Ser. No. 532,005, Sep. 14, 1983, Pat. No. 4,526,594, which is a continuation-in-part of Ser. No. 507,564, Jun. 24, 1983, Pat. No. 4,511,381, which is a continuation-in-part of Ser. No. 374,270, May 3, 1982, Pat. No. 4,421,535.

[51] Int. Cl.$^4$ ............................................. F25J 3/02
[52] U.S. Cl. ............................................ 62/17; 55/48; 55/51; 55/68; 62/20
[58] Field of Search ............ 62/9, 11, 17, 20, 23, 62/24, 27, 28, 41; 55/68, 69, 29, 30, 36, 38, 43, 46, 48, 51

[56] References Cited

U.S. PATENT DOCUMENTS

| | | |
|---|---|---|
| 1,786,521 | 6/1930 | Ayers . |
| 1,934,029 | 11/1983 | Asbury ................................ 23/210 |
| 2,187,631 | 1/1940 | Schutt ...................................... 196/9 |
| 2,226,467 | 12/1940 | Hjerpe et al. ........................ 260/683 |
| 2,241,716 | 5/1941 | Roberts, Jr. et al. ................. 196/10 |
| 2,282,549 | 5/1942 | Sullivan, Jr. et al. .................. 196/9 |
| 2,301,548 | 11/1942 | Koch ....................................... 196/9 |
| 2,308,856 | 9/1943 | Borden .................................. 196/10 |
| 2,325,379 | 7/1943 | Durrum ................................ 202/40 |
| 2,433,286 | 12/1947 | McKinnis ........................... 202/39.5 |
| 2,455,803 | 12/1948 | Pierotti ............................... 202/39.5 |
| 2,504,429 | 4/1950 | Latchum, Jr. . |
| 2,511,206 | 6/1950 | Hasche ................................ 260/679 |
| 2,516,507 | 7/1950 | Deming ............................... 183/115 |
| 2,573,341 | 10/1951 | Kniel ................................... 260/683 |
| 2,588,323 | 3/1952 | Kniel ................................... 260/677 |
| 2,596,785 | 5/1952 | Nelly, Jr. et al. ..................... 48/190 |
| 2,610,704 | 9/1952 | Patterson ............................ 183/115 |

(List continued on next page.)

OTHER PUBLICATIONS

Kniel et al., "Ethylene Purification by Absorption Pro-
(List continued on next page.)

*Primary Examiner*—Steven E. Warner
*Attorney, Agent, or Firm*—Depaoli & O'Brien

[57] ABSTRACT

A continuous process is disclosed for separating components of a hydrocarbon gas stream which are selected from the group consisting of hydrogen, nitrogen, methane, ethylene, ethane, higher saturated and unsaturated hydrocarbons, and mixtures thereof by countercurrently contacting the hydrocarbon gas stream with a physical solvent selected from the group consisting of: (1) paraffinic solvents having molecular weights ranging from 75 to 140 and UOP characterization factors ranging from 12.0 to 13.5, these factors being independent of the aromatic content of the paraffinic solvents, (2) naphthenic solvents having molecular weights ranging from 75 to 130 and UOP characterization factors ranging from 10.5 to 12.0, these factors being independent of the aromatic content of the naphthenic solvents, and (3) benzene and toluene, to produce an overhead stream which is at least rich in at least one of the components and a rich solvent bottoms stream; and by recovering the lean physical solvent from the rich solvent bottoms stream and recycling the recovered stream to the contacting of Step A.

20 Claims, 7 Drawing Sheets

U.S. PATENT DOCUMENTS

| | | | |
|---|---|---|---|
| 2,675,095 | 4/1954 | Bogart . | |
| 2,745,889 | 5/1956 | Johnston et al. | 260/677 |
| 2,765,635 | 10/1956 | Redcay | 62/122 |
| 2,780,580 | 2/1957 | Kniel | 196/8 |
| 2,804,488 | 8/1957 | Cobb, Jr. | 260/683 |
| 2,813,920 | 11/1957 | Cobb, Jr. | 260/683 |
| 2,849,371 | 8/1958 | Gilmore | 196/8 |
| 2,868,326 | 1/1959 | Gilmore | 183/115 |
| 2,887,850 | 5/1959 | Adams | 62/17 |
| 2,908,625 | 10/1959 | Mekler et al. | 208/54 |
| 2,938,865 | 5/1960 | Moyer | 208/341 |
| 2,959,540 | 11/1960 | Cahn et al. | 208/345 |
| 3,187,064 | 6/1965 | Wang et al. | 260/677 |
| 3,197,970 | 8/1965 | Nelson et al. | 62/17 |
| 3,213,151 | 10/1965 | Sherk | 260/667 |
| 3,291,849 | 12/1966 | King et al. | 260/672 |
| 3,349,145 | 10/1967 | Uitti | 260/672 |
| 3,383,838 | 5/1968 | Carson | 55/44 |
| 3,555,837 | 1/1971 | McClintock | 62/17 |
| 3,574,089 | 4/1971 | Forbes | 208/101 |
| 4,009,097 | 2/1977 | Ward | 208/302 |
| 4,072,604 | 2/1978 | Ward | 208/341 |
| 4,401,450 | 8/1983 | Schramm | 62/13 |
| 4,479,812 | 10/1984 | Hsia et al. | 55/48 |
| 4,552,572 | 11/1985 | Galstaun | 55/36 |
| 4,623,371 | 11/1986 | Mehra | 62/17 |
| 4,680,042 | 7/1987 | Mehra | 62/17 |
| 4,692,179 | 9/1987 | Mehra | 62/17 |
| 4,696,688 | 9/1987 | Mehra | 62/17 |
| 4,743,282 | 5/1988 | Mehra | 62/17 |

OTHER PUBLICATIONS cess", Chemical Engineering Progress, vol. 43, No. 7, pp. 335–342, Jul. 1947.

Kniel, "Propane Recovery by Absorption", Petroleum Refiner, vol. 27, No. 11, Nov. 1948.

Schutt et al., "How To Recover Ethylene", Oil and Gas Journal, Jul. 30, 1956, pp. 171–174.

Nelson, "Rebuilding Hydorcarbons", Petroleum Refinery Engineering, 4th Edition, p. 721, (McGraw-Hill).

"Gas Conditioning," Under Natural Gas in vol. 11 of *Kirk-Othmer Encyclopedia of Chemical Technology,* Third Edition, 1980, pp. 638–641.

"Humble's Avery Island Plant: High Safety at Low Cost", by J. J. Weatherby, *Hydrocarbon Processing & Petroleum Refiner,* Apr. 1962, vol. 41, No. 4, pp. 113–116.

"High $CO_2$-High $H_2S$ Removal with Selexol Solvent", by John W. Sweny, 59th Annual GPA Convention, Mar. 17–19, 1980 Houston, Tex.

"Gas Absorption", as Chapter 8 in *Mass Transfer Operations,* by Treybal, McGraw-Hill Book Company, Second Edition, 1968, pp. 221–226 and pp. 393–395.

"Absorption" Under Liquefied Petroleum Gas in vol. 14, of *Kirt-Othmer Encyclopedia of Chemical Technology,* Third Edition, 1980, pp. 383–388.

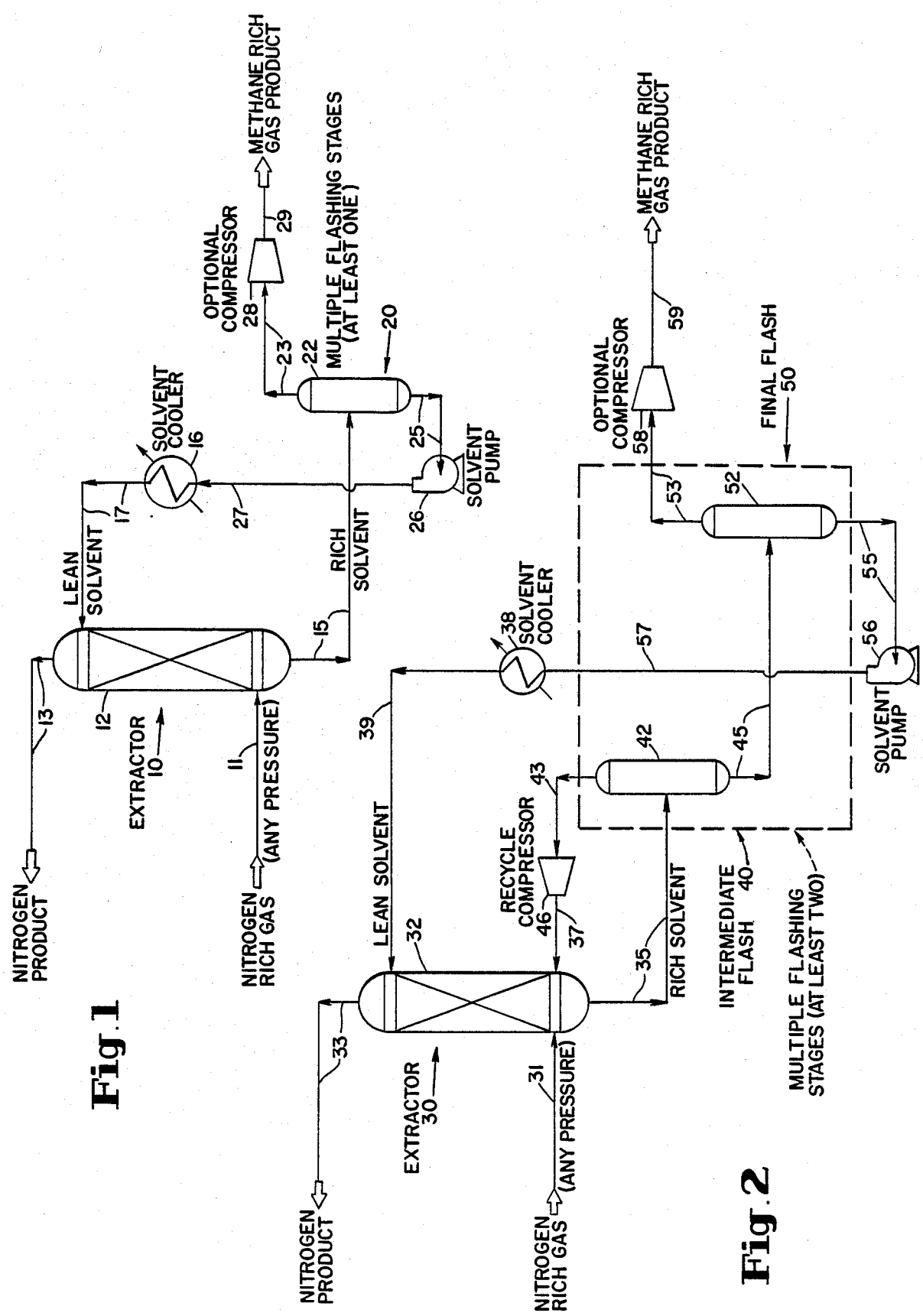

PROCESSING NITROGEN-RICH, HYDROGEN-RICH, AND OLEFIN-RICH GASES WITH PHYSICAL SOLVENTS

RELATED APPLICATIONS

This is a continuation-in-part of copending application Ser. No. 074,226, filed July 16, 1987, pending which is a continuation-in-part of copending application Ser. No. 024,561, filed Mar. 11, 1987, pending which is a continuation-in-part of co-pending application Ser. No. 854,383, filed Apr. 21, 1986, pending which is a continuation-in-part of co-pending application Ser. No. 828,996, filed Feb. 13, 1986, issuing as U.S. Pat. No. 4,696,688, and of application Ser. No. 828,988, filed Feb. 13, 1986 and now U.S. Pat. No. 4,680,042, which are continuations-in-part of application Ser. No. 808,463, filed Dec. 13, 1985, now U.S. Pat. No. 4,692,179, which is a continuation-in-part of application Ser. No. 784,566, filed Oct. 4, 1985, now U.S. Pat. No. 4,817,038, which is a continuation-in-part of application Ser. No. 759,327, filed July 26, 1985, now U.S. Pat. No. 4,623,371, which is a continuation-in-part of application Ser. No. 758,351, filed July 24, 1985, now U.S. Pat. No. 4,601,738, which is a continuation-in-part of application Ser. No. 637,210, filed Aug. 3, 1984, now U.S. Pat. No. 4,578,094, which is a continuation-in-part of application Ser. No. 532,005, filed Sept. 14, 1983, now U.S. Pat. No. 4,526,594, which is a continuation-in-part of application Ser. No. 507,564, filed June 24, 1983, now U.S. Pat. No. 4,511,381, which is a continuation-in-part of application Ser. No. 374,270, filed May 3, 1982, now U.S. Pat. No. 4,421,535.

BACKGROUND OF THE INVENTION

1. Field of the invention

This invention relates to processing a natural gas, a thermally or catalytically cracked gas, or a refinery off gas to produce a methane-rich product, a nitrogen-rich product, a hydrogen-rich stream, or an olefins-rich product therefrom by solvent extraction. It further relates to adapting the extractive flashing and the extractive stripping versions of the Mehra process for processing of such gas streams by using selected physical solvents.

2. Review of the Prior Art

Many hydrocarbon gases, such as natural gas, are contaminated with one or more inert gases which lower their heat content or otherwise impair their marketability. Such inert gases include nitrogen, helium, and argon. Contamination of natural gas with nitrogen is particularly common. Nitrogen may be a natural component or may be caused by nitrogen injections for reviving oil wells in suitable formations, such as in the central and north Texas areas of the United States.

Such contamination by nitrogen has caused the oil producer to curtail oil production because government regulations prevent him from burning the nitrogen-rich associated gas, and both environmental laws and a desire to preserve valuable resources prohibit him from venting the associated hydrocarbons. The oil producer is thus limited by the choice of technology available to him for properly processing the associated gases from an oil well. The prior art technology, which involves cryogenic principles, cannot economically process the natural gas streams which contain more than 3 mol % nitrogen even after subsidization with the revenue from oil production.

Olefins such as ethylene and propylene are present in thermally or catalytically cracked gas streams or in refinery off gases and are commonly associated with large quantities of hydrogen. These gases generally comprise methane, carbon monoxide, carbon dioxide, acetylene, ethane, methyl acetylene, propadiene, propylene, propane, butadienes, butenes, butanes, $C_5$'s, $C_6$–$C_8$ non-aromatics, benzene, toluene, xylenes, ethyl benzene, styrene, $C_9$–400° F. gasoline, 400+° F. fuel oil, and water.

Numerous processes are known in the solvent absorption art for isolation and recovery of olefins from cracked, refinery, and synthetic gases containing these unsaturated compounds. Some processes utilize specific paraffinic compounds as an absorption oil, and others utilize an aromatic absorption oil as a solvent within an absorber column or an absorber-stripper column having a reboiler. In some instances, these processes additionally isolate a methane-rich stream and/or a hydrogen-rich stream.

A wide variety of gaseous streams are to be found in petroleum refineries. Some streams are integral parts of a specific process, e.g., they are recycled from a fractionating column to a reactor. Such a recycle stream may be an impure hydrogen stream which must be purified before returning to the reactor and/or combining with a make-up hydrogen stream. Other such gaseous streams may be a byproduct of a major refinery process and may be sent to one or more other processes which are nearby and require a hydrogen feed stream. As crudes having higher sulfur content and higher carbon-to-hydrogen ratio continue to be processed and as stricter environmental regulations requiring lower sulfur content are passed, the hydrogen demand is expected to grow. Even though a substantial portion of this increased demand will be met by steam reforming of light hydrocarbons and partial oxidation of heavy hydrocarbons, upgrading of existing off-gas streams is a viable alternative.

For example, the byproduct hydrogen stream from an ethylene cracking plant may have a hydrogen content of 75 mol % and may be initially needed as feed to a hydrodealkylation process requiring 95 mol % hydrogen. Or a change in process conditions at a nearby hydroforming plant may create a demand for 99 mol % hydrogen and consequent purification of a 90% hydrogen byproduct stream, for example, that happens to be available.

There is clearly a need in such circumstances to be able to change selectively from one hydrogen purity to another without having to change equipment specifications.

There are many small to medium size off-gas streams that contain hydrogen and heavier hydrocarbons which are currently being sent to the fuel systems of petroleum refineries. A summary of various hydrogen source streams containing approximate concentrations of hydrogen as published in *Oil and Gas Journal*, Feb. 6, 1984, p. 111, by Wang et al is shown in Table I. In most of the refinery and petrochemical applications where hydrogen is used as a reactant, the desired makeup hydrogen has a purity of about 95%. In order to prevent the build-up of reaction byproducts, such as methane, a portion of the recycle stream is customarily purged. Even though such a stream is relatively small, its concentration of hydrogen represents a loss which must be offset by additional hydrogen makeup.

TABLE I

Sources of Hydrogen Off-Gas Streams

| Industry | Source | Approximate Hydrogen Concentration |
|---|---|---|
| Refining | HT Purge | 25–35 |
|  | FCC Gas | 10–15 |
|  | Cascade Reject | 50–60 |
| Methanol | Purge Gas | 70–80 |
| Ethylene | By-Product $H_2$ | 60–90 |
|  | Cracked Gas | 10–35 |
| Coke Oven | Product Gas | 0–5 |
| LPG Dehydrogenation | Product Gas | 58 |
| Toluene HDA | $H_2$ Purge | 57 |
| Cyclohexane | $H_2$ Purge | 42 |
| Carbon Black | Product Gas | 7 |
| Formaldehyde | By-product $H_2$ | 18 |
| Ammonia | Purge Gas | 60 |

Several processes have been used and are currently available for upgrading the quality of such off-gas streams. These processes, as described by Wang et al in the *Oil and Gas Journal* article of Feb. 11, 1984, include cryogenic separation, catalytic purification, pressure swing adsorption, and membrane separation. Selection of a suitable process depends upon many factors, some of which are the hydrogen product purity that is desired, hydrogen recovery levels, available pressure drop, pretreatment requirements, off-gas composition, impact of reaction products remaining in the hydrogen product, and turndown capability of the selected process.

The bulk of the industrial hydrogen manufactured in the United States uses the process of steam reforming of natural gas according to the equation $2CH_4 + 3H_2O \rightarrow CO + CO_2 + 7H_2$. Other processes utilize partial oxidation of resids, coal gasification, and water hydrolysis, but when proceeding from natural gas to liquid hydrocarbons and then to solid feed stocks, the processing difficulties and manufacturing costs increase.

The impurities usually found in raw hydrogen are $CO_2$, $CO$, $O_2$, $N_2$, $H_2O$, $CH_4$, $H_2S$, and higher hydrocarbons. These impurities can be removed by shift catalysis, $H_2S$ and $CO_2$ removal, PSA process, and nitrogen wash. Upgrading of various refinery waste gases is nearly always more economical than hydrogen production by steam reforming. Composition of the raw gas and the amount of impurities that can be tolerated in the product generally determine the selection of the most suitable process for purification.

U.S. Pat. No. 2,187,631 relates to producing unsaturated $C_4$ and $C_5$ hydrocarbons by viscosity breaking a heavy resid and thermally cracking the low-boiling oil fraction thereof in combination with a recycle oil to produce conversion products which are fractionated to isolate a light gas-vapor fraction containing unsaturated and aromatic hydrocarbons desired as final products. This fraction is subjected to a selective absorption operation with an aromatic absorption oil which primarily absorbs the di-olefins and the branched chain mono-olefins of $C_4$ and $C_5$ saturated and unsaturated hydrocarbons.

U.S. Pat. No. 2,282,549 relates to polymerizing gaseous olefins to light hydrocarbons of gasoline-like character, with or without catalysis. Solvent scrubbing is used to eliminate ethane, hydrogen, etc. by contacting an olefinic gas mixture containing up to 50% of olefins with a solvent at 100–1000 psi so that hydrogen and $C_1+$ hydrocarbons remain undissolved and can be separated from the scrubbing oil containing dissolved olefinic hydrocarbons. The solvent may be "condensed and thermally stable aromatic hydrocarbons, such as diphenyl, or polymerization products boiling higher than gasoline and produced in the system itself". The solvent must have a high solvent power for the gaseous olefins and relative low solvent power for methane and hydrogen at 100–1000 psi.

U.S. Pat. No. 2,308,856 relates to a continuous process for extracting olefins from gaseous mixtures by countercurrent contact with a selective solvent for olefins such as isoamylether and other higher aliphatic ethers, butylether, amylether, and similar compounds. The solvent is preferably cooled to a temperature of $-20°$ C. to $25°$ C., depending upon the solvent and the type of gases to be extracted. The pressure in the absorber may vary from 50 to 300 psi.

U.S. Pat. No. 2,325,379 teaches a process for separating a liquid mixture of components by extractive distillation in the presence of a relatively high boiling selective solvent which may be a polar solvent.

U.S. Pat. No. 2,433,286 is directed to extractive distillation of liquid hydrocarbon mixtures with paraffin hydrocarbons as the extraction solvent in a first extractive distillation to produce olefins plus diolefins in the rich solvent and in a second extractive distillation with unsaturated or aromatic hydrocarbons as the solvent at a higher temperature to produce olefins as the raffinate and diolefins in the rich solvent. Paraffins are distilled from the rich solvent of the first extractive distillation and diolefins are distilled from the rich solvent of the second extractive distillation.

U.S. Pat. No. 2,455,803 describes a process for extractive distillation of a vaporizable organic mixture with a solvent comprising (1) a selective solvent and (2) a mutual solvent for the selective solvent and the mixture. The selective solvent must have high selectivity which is frequently coupled with low solvent power, thereby tending to form two liquid layers within the extractor. The purpose of the mutual solvent is to maintain a single liquid phase. The presence of the solvents in the mixture must cause a greater change in the "escaping tendency" of one component of the mixture relative to that of the other components, "escaping tendency" being defined as the potential of one component to pass from one phase to another. Solvents such as furfural and phenol are named as those having preferential solvent power for aromatic over paraffinic hydrocarbons. Suitable mutual solvents are identified as methyl ketone, cyclohexanone, lactonitrile, morpholine, and aromatic hydrocarbons such as benzene, toluene, cumene, mesitylene, and the like.

U.S. Pat. No. 2,511,206 describes a process for producing commercially valuable ethylene in a derivative of acetylene by pyrolytic decomposition of a hydrocarbon to form a complex gaseous mixture containing ethylene, propylene, and acetylene, then absorbing propylene and acetylene in a polyethylene glycol ether to remove a residual gas containing ethylene, stripping the absorbing medium containing the acetylene and propylene to produce a secondary gas containing propylene and acetylene, and finally processing the secondary gas to produce the desired derivative of acetylene.

U.S. Pat. No. 2,516,507 is relevant for its use of an extractive stripper column for separating a gaseous mixture consisting essentially of $C_1$, $C_2$, and $C_3$ hydrocarbons, including ethylene, by countercurrent absorption in a $C_5$–$C_7$ hydrocarbon as absorbent oil. The process is suitably conducted at 80° F. and a pressure of 300 psia. In the extractive distillation column containing a reboiler, there are successive absorption zones for propane, $C_2$-hydrocarbons, and methane. When the gaseous mixture to be separated is a wet hydrocarbon gas feed, e.g., such as a wet gas from an oil well or a refinery off-gas comprising $C_1$–$C_4$ hydrocarbons with $N_2$ and/or $H_2$, the rate of feeding the lean oil to the column may be adjusted in relation to the composition of the feed, the nature of the absorption oil, and the temperature and the pressure in the column so that substantially all the $C_3$ materials are absorbed in the propane absorption zone (primary) while a substantial proportion of the gas at the top of the primary zone is withdrawn as a $C_2$-concentrate. The proportion withdrawn is selected so that as remaining gas contacts the oil in the $C_2$ or secondary absorption zone, substantially all of the $C_2$ content thereof is absorbed in the oil and is thereby returned to the $C_3$ absorption zone from which it is stripped by the as yet unabsorbed $C_3$ therein. Similarly, methane and lighter components are withdrawn from the top of the $C_2$ (secondary) absorption zone, and the methane and lighter components in the remaining gas, when contacted by the lean oil entering at the top of the column, are stripped of methane, leaving hydrogen and nitrogen to leave the column as the overhead stream.

U.S. Pat. No. 2,573,341 relates to recovering olefinic hydrocarbons from refinery off-gases comprising hydrogen in continuous absorber-stripper columns, using aromatic absorption oil at super-atmospheric pressure. Methane, the lighter hydrocarbons, and hydrogen form the overhead from the first column, and ethylene and heavier fractions are in the fat oil. Successively operated columns separate the olefins.

U.S. Pat. No. 2,588,323 describes an absorption process, for recovering olefins from refinery off-gases, which employs an aromatic absorber oil. The process is very similar to the process of U.S. Pat. No. 2,573,341 except that methanol is added to the overhead of both the ethylene fractionator and the de-ethanizer column and is also fed to one or more of the upper intercoolers of the rectifying-absorber column.

U.S. Pat. No. 2,610,704 relates to contacting refinery gas mixtures, typically comprising hydrogen, methane, ethylene, and ethane, with a polar, preferably water soluble, liquid solvent to depress the volatility of ethylene, relative to hydrogen and methane, in a distillation zone within an extractive distillation column. Temperature and pressure were found to be interrelated. Preferably, temperatures are from 0°–120° F. and pressures from 200–300 psi. The solvent may be an aqueous acetone solution containing 96% acetone and 4% water at a ratio of about 2.5–3.5 of solvent to hydrocarbon at the top of the column. The distillate material in the overhead is typically an admixture of hydrogen and methane, substantially all of the ethylene being in the rich solvent. The rich solvent is flashed at a pressure of about 5 psi to vaporize most of the ethylene. The flashed solvent is then stripped of the remaining ethylene by heating. Finally, the recovered ethylene is washed with water to recover solvent vapors.

U.S. Pat. No. 2,780,580 describes a process for countercurrently treating pyrolysis gas with lean oil, having a boiling range of 100°–400° F. The process utilizes a primary absorber for partial recovery of ethane and a secondary absorber to which pyrolysis gas is fed in the midsection thereof and to which both the bottoms of the primary absorber and fresh lean oil are also fed, producing a fat oil which is sent to a distillation column for removing $C_2$ and to produce a rich oil which is fed to another distillation column to remove $C_3$. The lean oil circulation is controlled so that upwards of 75% of the ethylene entering the secondary absorber is recovered with the fresh lean oil while not over 75% of the ethane is recovered by the same lean oil fed to the primary absorber.

U.S. Pat. No. 2,804,488 is relevant for its employment of an absorber-stripper and two absorbents (lean oil and ethane) in the recovery of ethylene from a stream of cracked gas. After compression to 180 psi at 45° F., the lean oil removes $C_5+$ hydrocarbons from the cooled and compressed gas in an absorption zone, producing an overhead gas stream which is dried, cooled to −148° F., and passed countercurrently within a demethanizing absorber to an ethane stream. The overhead from the absorber is composed of uncondensed gases. The rich absorbent may be stripped of methane by distillation in a methane stripper and then split within an ethylene fractionator into a solvent stream (ethane) and an ethylene/acetylene overhead stream which is split by partial condensation into separate acetylene and ethylene streams.

U.S. Pat. No. 2,849,371 describes a process for separating and recovering low boiling components of a natural gas or of a refinery or synthetic gas which is fed to the midsection of an absorber-stripper column to which the lean absorption oil is fed at the top thereof. This absorbent oil is butane at about 60° F. The off-gas from the absorber-stripper column is fed to a secondary absorber to which debutanized gasoline is fed as the absorbent oil at the top thereof to extract the relatively high boiling hydrocarbons and produce a residue gas. The bottoms material from the absorber-stripper column is fed to a depropanizer, and the overhead therefrom is fed to a de-ethanizer.

An absorption process is disclosed in U.S. Pat. No. 3,213,151 for recovering a recycle stream of 50% hydrogen from a gaseous mixture, comprising hydrogen, methane, and normally liquid hydrocarbons, by absorption with pentanes.

A process is disclosed in U.S. Pat. No. 3,291,849 in which toluene, mixed with other alkyl benzenes, is produced as a lean oil which is used in an absorber to purify a make-up hydrogen stream from a catalytic reformer.

U.S. Pat. No. 3,349,145 teaches an improvement in a process for the catalytic hydrodealkylation of an alkyl aromatic hydrocarbon feed in the presence of an excess of hydrogen. The process comprises withdrawing a hydrogen-rich gas from a source of impure hydrogen, containing 50–90 mol % hydrogen, the remainder being $C_1$–$C_6$ paraffins, and countercurrently scrubbing the gas, which is under a pressure of 200–1000 p.s.i.g. and at a temperature below 200° F., with a liquid absorbent consisting essentially of a mixture of $C_9+$ aromatic hydrocarbons, thereby absorbing a substantial portion of the paraffins in the absorbent. The aromatic hydrocarbons utilized as the liquid absorbent may comprise, either in pure form or in admixture with other aromatics, xylenes and hgher polyalkyl benzenes such as trimethylbenzenes and tetramethylbenzenes. However, alkyl-substituted mononuclear aromatics, having more than three methyl groups per nucleus or having an alkyl group containing more than three carbon atoms, are less preferred because of their higher hydrogen equivalency. When the crude hydrogen contains $C_6$, $C_7$, or $C_8$ paraffins, a preferred absorbent comprises a $C_{9+}$ aromatic hydrocarbon, either in pure form or admixed with other $C_{9+}$ aromatics, such as propylbenzene, isopropylbenzene, pseudocumene, and mesitylene.

U.S. Pat. No. 4,479,812 provides a continuous fractionation technique for recovering ethylene from an olefinic feedstock comprising $C_{3+}$ higher olefins by contacting the olefinic feedstock countercurrently with a liquid solvent stream comprising $C_{6+}$ olefinic gasoline range hydrocarbons for selectively absorbing substantially the entire $C_{3+}$ olefin components from the feedstock and then withdrawing an ethylene-rich vapor stream from the absorption tower and further contacting the ethylene-rich stream with a distillate range liquid hydrocarbon stream in a sponge absorber to purify the ethylene stream. The absorption tower is an absorber-stripper column having two intercoolers and a reboiler.

U.S. Pat. No. 4,552,572 relates to purification of raw gases derived from coal by high temperature gasification. Suitable purification solvents must have preferential selectivity for hydrogen sulfide over carbon dioxide. They include methanol, N-methyl pyrrolidone, and dimethyl ether of polyethylene glycol. Commonly, the raw gas intended for synthesis is divided into two parts, one of which is passed through a shift reactor to convert a major portion of its cabon monoxide to hydrogen by the shift reaction: $CO + H_2O \rightarrow CO_2 + H_2$. As the purification treatments remove impurities, including $CO_2$, the shifted gas, which is rich in hydrogen, and the ushifted gas, which is rich in carbon monoxide, may be blended to produce the ratio of hydrogen to carbon monoxide required for a specific synthesis.

An improved extractive flashing version and an improved extractive stripping version of the Mehra Process are respectively described in U.S. Pat. Nos. 4,623,371 and 4,680,042 for separating $C_{2+}$ hydrocarbons from a nitrogen-rich hydrocarbon gas containing from 3 to 75 mol % nitrogen, the remainder being hydrocarbons.

Additional Mehra Process applications for processing nitrogen-rich, hydrogen-rich, and olefin-containing gas streams have been described in an article by Yuv R. Mehra entitled "Using Extraction to Treat Hydrocarbon Gases", *Chemical Engineering*, Oct. 27, 1986, in a paper presented by Yuv R. Mehra entitled "Mehra Process Flexibility Improves Gas Processing Margins" at the 66th Annual Convention of the Gas Processors Association, Mar. 16-18, 1987 at Denver, Colo., in a paper presented by Yuv R. Mehra at the 1987 National Petroleum Refiners Association's Annual Meeting in San Antonio, Tex., Mar. 29-31, 1987, entitled "Recover and Purify Hydrogen Economically", and in an article published in AIChE's *Energy Progress,* September 1987, page 150, entitled "New Process Flexibility Improves Gas Processing Margins", by Yuv R. Mehra.

SUMMARY OF THE INVENTION

It has surprisingly been discovered that certain paraffinic and naphthenic solvents possess higher solubilities than the aromatic and other preferential physical solvents described in the following U.S. Pat. Nos. of Yuv R. Mehra: 4,421,535, 4,511,381, 4,526,594, 4,578,094, 4,601,738, 4,617,038, 4,623,371, 4,692,179, 4,680,017, and 4,696,688. These patents are hereby incorporated herein by reference.

The following applications of Yuv R. Mehra are also hereby incorporated by reference: Ser. Nos. 06/828,996; 06/854,383; 07/024,561; and 07/074,226.

It is accordingly an object of this invention to provide combinations of selected solvent extraction processes for gas mixtures with certain solvents selected according to novel criteria and further with selected pressure, temperature, solvent flow rate, and gas flow rate conditions to produce desired recoveries of selected components of the gaseous mixtures under economical construction and operating conditions.

It is also an object to apply these solvent selection criteria to processes for treating nitrogen-rich gases, hydrogen-rich gases, and olefin-rich gases. This invention is based upon the discovery that the paraffinic, naphthenic, and lighter aromatic solvents offer significant potential for (a) lower initial capital investment and (b) lower ongoing operating costs because it has been found that higher solubility properties outweigh outstanding selectivity properties on a cost basis. Specifically, lower selectivities can be compensated for by additional height in an extraction column, whereas lower solubilities can only be compensated for by greater column diameters and higher solvent flow rates, causing higher capital and operating costs.

These selection criteria, whether they are applicable to a mixture of compounds or to a pure compound, are the molecular weight and the UOP characterization factor for each solvent. Paraffinic solvents, naphthenic solvents, and lighter aromatic solvents have distinctive ranges for each criterion.

For the purposes of this invention, as shown in Table II, all physical solvents from the group of paraffinic and naphthenic solvents having molecular weights ranging from 75 MW to 140 MW, plus benzene and toluene among the aromatic group, are considered to be useful additional solvents for the Mehra Process. This group of paraffinic solvents is additionally defined as solvents having UOP characterization factors ranging from 12.0 to 13.5. The naphthenic solvents are defined as those having UOP characterization factors ranging from 10.5 to 12.0. Both of these definitions are independent of the solvent's aromatic contents.

When the molecular weight of each paraffinic solvent is less than 75, solubility in the solvent is at its highest, but the cost of separating the product from the solvent, as in the product column, fractionator, or regenerator, becomes prohibitive. Further, systems using solvents of molecular weight less than 75 inherently require a solvent recovery system.

TABLE II

| | | | | AVG. | ASTM D-86 DISTILLATION TEMPERATURES, | | | | | | | | | | | | |
|---|---|---|---|---|---|---|---|---|---|---|---|---|---|---|---|---|---|
| | | | UOP | BP | °F., AT INDICATED PERCENTAGES OF FEED DISTILLED | | | | | | | | | | | | |
| Type | MW | S.G. | API | K | °F. | IBP | 5% | 10% | 20% | 30% | 40% | 50% | 60% | 70% | 80% | 90% | 95% | EP |
| Paraffinic | 75 | 0.6436 | 88.36 | 12.7 | 98 | 70 | 88 | 91 | 93 | 96 | 97 | 98 | 100 | 101 | 104 | 110 | 124 | 174 |
| Paraffinic | 85 | 0.6566 | 84.00 | 12.8 | 136 | 106 | 125 | 128 | 131 | 134 | 135 | 136 | 138 | 140 | 142 | 149 | 163 | 217 |

TABLE II-continued

| | | | | AVG. | ASTM D-86 DISTILLATION TEMPERATURES, | | | | | | | | | | | | |
|---|---|---|---|---|---|---|---|---|---|---|---|---|---|---|---|---|---|
| | | | UOP | BP | °F., AT INDICATED PERCENTAGES OF FEED DISTILLED | | | | | | | | | | | | |
| Type | MW | S.G. | API | K | °F. | IBP | 5% | 10% | 20% | 30% | 40% | 50% | 60% | 70% | 80% | 90% | 95% | EP |

TYPICAL MEHRA PROCESS SOLVENT CHARACTERISTICS

| Type | MW | S.G. | API | UOP K | AVG. BP °F. | IBP | 5% | 10% | 20% | 30% | 40% | 50% | 60% | 70% | 80% | 90% | 95% | EP |
|---|---|---|---|---|---|---|---|---|---|---|---|---|---|---|---|---|---|---|
| Paraffinic | 100 | 0.6830 | 75.67 | 12.7 | 194 | 161 | 182 | 185 | 188 | 191 | 193 | 194 | 196 | 198 | 201 | 208 | 224 | 283 |
| Paraffinic | 110 | 0.6992 | 70.87 | 12.6 | 234 | 199 | 222 | 225 | 228 | 231 | 233 | 234 | 236 | 238 | 241 | 249 | 266 | 328 |
| Paraffinic | 120 | 0.7130 | 66.96 | 12.6 | 270 | 233 | 257 | 261 | 263 | 267 | 269 | 270 | 272 | 274 | 277 | 286 | 304 | 369 |
| Paraffinic | 130 | 0.7231 | 64.19 | 12.6 | 302 | 263 | 288 | 292 | 295 | 299 | 301 | 302 | 304 | 307 | 310 | 319 | 337 | 406 |
| Paraffinic | 140 | 0.7322 | 61.75 | 12.6 | 328 | 288 | 314 | 318 | 321 | 325 | 327 | 328 | 330 | 332 | 336 | 345 | 365 | 435 |
| Naphthenic | 75 | 0.7569 | 55.46 | 11.0 | 124 | 94 | 113 | 116 | 119 | 122 | 123 | 124 | 126 | 128 | 130 | 137 | 151 | 203 |
| Naphthenic | 85 | 0,7689 | 52.53 | 11.1 | 169 | 137 | 158 | 161 | 163 | 166 | 168 | 169 | 171 | 173 | 175 | 183 | 198 | 255 |
| Naphthenic | 110 | 0.7843 | 48.92 | 11.4 | 260 | 223 | 247 | 251 | 254 | 257 | 259 | 260 | 262 | 264 | 267 | 276 | 293 | 358 |
| Naphthenic | 130 | 0.7960 | 46.26 | 11.4 | 290 | 252 | 276 | 280 | 283 | 287 | 289 | 290 | 292 | 295 | 298 | 307 | 324 | 392 |
| Benzene | 78 | 0.8845 | 28.48 | 9.7 | 176 | | | | | | | | | | | | | |
| Toluene | 92 | 0.8719 | 30.79 | 10.1 | 231 | | | | | | | | | | | | | |
| Ethylbenzene | 106 | 0.8717 | 30.83 | 10.4 | 277 | | | | | | | | | | | | | |
| m-Xylene | 106 | 0.8688 | 31.37 | 10.4 | 282 | | | | | | | | | | | | | |
| Mesitylene | 120 | 0.8709 | 30.98 | 10.6 | 332 | | | | | | | | | | | | | |
| Pseudo-cumene | 120 | 0.8811 | 29.09 | 10.5 | 339 | | | | | | | | | | | | | |

When the molecular weight of a paraffinic solvent exceeds 140, or when the molecular weight of a naphthenic solvent exceeds 130, these solvents no longer exhibit an improvement in solubility relative to preferential physical solvents previously disclosed in issued Mehra patents and pending Mehra patent applications.

Depending upon the selected physical solvent and on the economics of a given facility, it may also be necessary to provide a solvent recovery system. Refrigeration, adsorption, and/or a sponge oil system may be utilized.

As defined in pages 102-104 of "Petroleum Refinery Engineering," by W. L. Nelson, second edition, McGraw-Hill Book Co., Inc., New York, 1941, the UOP characterization factor, K, is useful in cataloging crude oils and is even more valuable for defining the degree of paraffinicity of individual fractions. It has also been useful in correlating many properties, such as hydrogen content, aniline point, thermal expansion, viscosity index, and latent heat. It should be noted that if the values of any two of these properties are known, the values of the other properties can be determined. This UOP "K" characterization factor may also be described as an index of the chemical character of pure hydrocarbons and petroleum fractions. The characterization factor of a hydrocarbon is defined as the cube root of these absolute average boiling point in degrees R (°F. +460°) divided by its specific gravity (60° F./60° F.); i.e., the characterization factor equals:

$$K = \frac{\sqrt[3]{T_B}}{s}$$

where
$T_B$ = average boiling point, °R.
s = specific gravity at 60° F.

As useful as this characterization factor is, however, it should be borne in mind that it is only an approximate index of the chemical nature of hydrocarbons, as indicated by its variation with boiling point, both for members of a homologous series and for petroleum fractions.

BRIEF DESCRIPTION OF THE DRAWINGS

FIG. 1 is a schematic flow sheet for contacting a nitrogen-rich gas at any pressure with a lean physical solvent to produce a nitrogen product and a methane-rich gas product after at least one flashing stage.

FIG. 2 is a similar schematic flow sheet for contacting a nitrogen-rich gas at any pressure with a lean physical solvent to produce a nitrogen product as overhead and the methane rich gas product from the rich bottoms solvent after a succession of at least two flashes, the overhead gas from the first flash being recycled to the extractor column.

DESCRIPTION OF THE PREFERRED EMBODIMENTS

Figure 3:
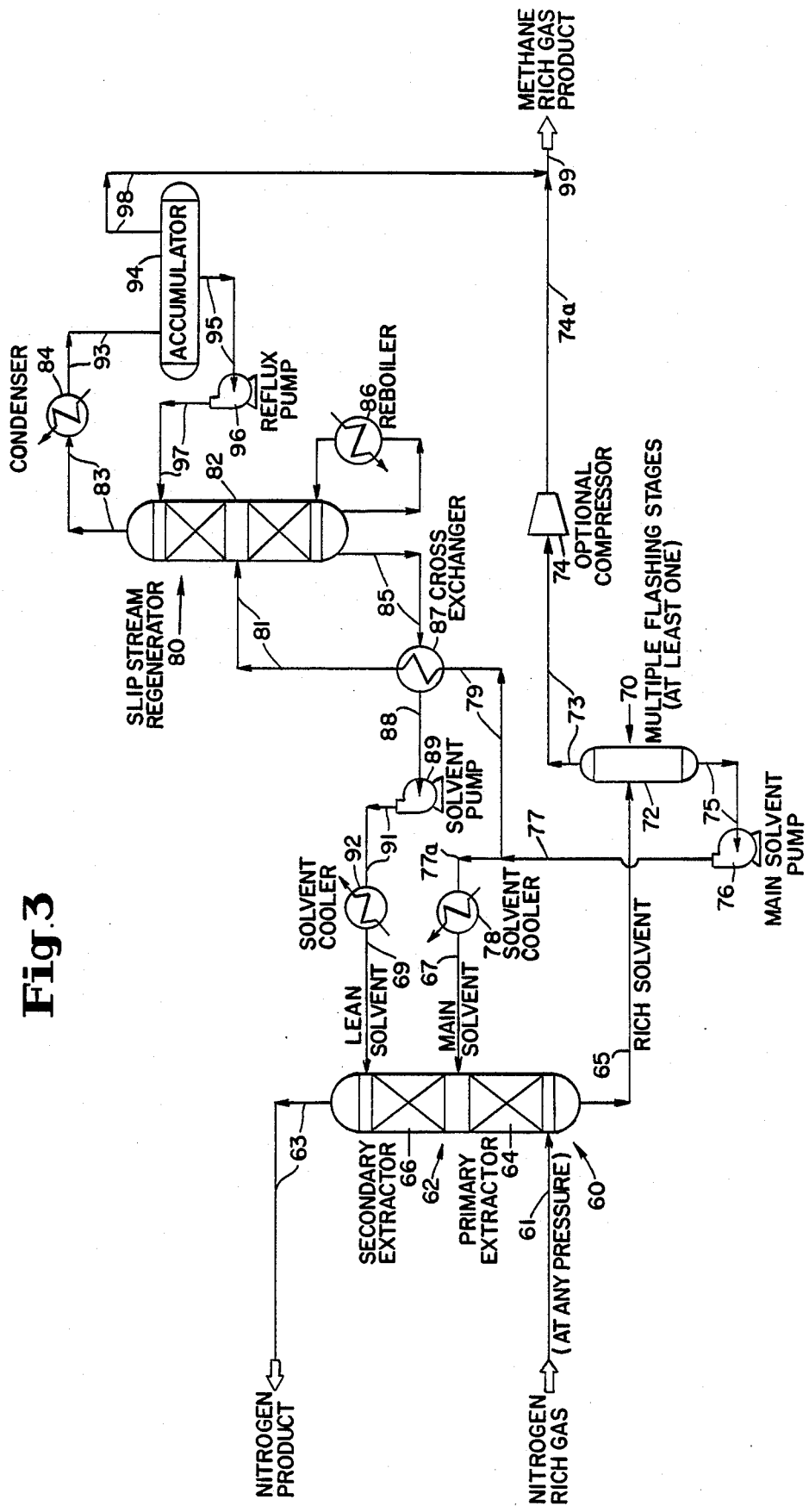
FIG. 3 is another schematic flow sheet for contacting a nitrogen-rich gas at any pressure with a main stream of stripped solvent entering the midsection of an extractor column and with a cleanup stream of lean-and-dry solvent entering the top of the column to produce a nitrogen product as overhead and a methane-rich gas product from the rich bottoms solvent stream after at least one flashing stage, the stripped solvent being split into the main solvent stream and into a slipstream which is regenerated in a regenerator column to produce stripped gases as its overhead stream, these gases being added to the methane-rich gas product.

It should be understood that pipelines are in fact being designated when streams are identified hereinafter and that streams are intended, if not stated, when materials are mentioned. Moreover, flow-control valves, temperature regulatory devices, pumps, and the like are to be understood as installed and operating in conventional relationships to the major items of equipment which are shown in the drawings and discussed hereinafter with reference to the continuously operating process of this invention. All of these valves, devices, and pumps, as well as heat exchangers, accumulators, condensers, and the like, are included in the term, "auxiliary equipment". The term, "absorber", is conventionally employed for a gas/solvent absorbing apparatus, but when it is utilized in the process of this invention with a physical solvent, it is considered to be an "extractor".

Nitrogen Rejection

The performance of various physical solvents for the nitrogen-methane system at 500 psia and $-10°$ F. is summarized in Table III, wherein the inlet gas contains 15 mol % $N_2$ and 85% mol % $C_1$. The conditions of pressure, temperature, and composition represent one of the many commercial applications and are selected only for demonstration of this invention. This invention is not to be construed as limited to these conditions.

Table III contains the actual molecular weights of five aromatic compounds and eleven exemplary molecular weights of paraffinic and naphthenic compounds. It also displays the required solvent flow rates in U.S. gallons per minute to achieve a 25% recovery of methane in the rich solvent by contacting 1,000 lb-mols per hour of the gas, consisting of 15% nitrogen and 85% methane, with the indicated solvent at the listed solvent/feed (S/F) molar ratio. Table III also contains the solubility ($\gamma$) of methane in each solvent, in standard cubic feet per gallon (SCF/gal), and the alpha ($\alpha$) ratio of hydrogen volatility to methane volatility from the solvent. It further contains the preferential factor ($\gamma \times \alpha$) for each solvent.

The selectivity of benzene solvent (78 MW) of 6.56, defined as its $KN_2/KC_1$ alpha value, is greater than that of the comparable paraffinic solvent (75 MW) of 3.97 by about 65.2%. However, the solubility of methane in the paraffinic solvent of comparable molecular weight requires a solvent circulation of 192 gpm for the paraffinic solvent which is significantly less than the circulation required by the benzene solvent of about 364 gpm, i.e., a reduction of about 47%.

TABLE III

PHYSICAL SOLVENT PERFORMANCE
NITROGEN-METHANE SYSTEM

BASIS: 1000 LB-MOL/HR FEED CONTAINING 15% N2 AND 85% C1
25% RECOVERY OF METHANE IN SOLVENT @ 500 PSIA & $-10°$ F.
STP = 14.696 psia @ 60° F.

| TYPE | SOLVENT MW | GAL/MIN STP | C1 SCF/GAL | ALPHA N2/C1 | PREF. FACTOR | S/F RATIO GAL/SCF |
|---|---|---|---|---|---|---|
| Paraffinic | 75 | 192 | 6.99 | 3.97 | 27.72 | 0.0304 |
| Paraffinic | 85 | 216 | 6.22 | 3.89 | 24.21 | 0.0342 |
| Paraffinic | 100 | 256 | 5.25 | 3.83 | 20.13 | 0.0405 |
| Paraffinic | 110 | 283 | 4.75 | 3.76 | 17.89 | 0.0447 |
| Paraffinic | 120 | 310 | 4.34 | 3.69 | 16.01 | 0.0490 |
| Paraffinic | 130 | 333 | 4.03 | 3.60 | 14.52 | 0.0526 |
| Paraffinic | 140 | 359 | 3.74 | 3.55 | 13.27 | 0.0568 |
| Naphthenic | 75 | 238 | 5.65 | 5.10 | 28.77 | 0.0376 |
| Naphthenic | 85 | 265 | 5.06 | 4.94 | 24.99 | 0.0419 |
| Naphthenic | 110 | 328 | 4.10 | 4.49 | 18.40 | 0.0518 |
| Naphthenic | 130 | 388 | 3.47 | 4.41 | 15.29 | 0.0613 |
| Benzene | 78 | 364 | 3.69 | 6.56 | 24.20 | 0.0576 |
| Toluene | 92 | 381 | 3.53 | 6.65 | 23.45 | 0.0603 |
| Ethylbenzene | 106 | 343 | 3.92 | 5.01 | 19.61 | 0.0543 |
| m-Xylene | 106 | 348 | 3.86 | 5.02 | 19.41 | 0.0550 |
| Mesitylene | 120 | 395 | 3.40 | 4.82 | 16.39 | 0.0624 |

From Mehra's earlier teachings, one would expect the paraffinic solvent to be about 14.6% better than the benzene solvent because the preferential factor, defined by the multiplication of alpha ($KN_2/KC_1$) with the solubility of methane in solvent (SCF of $C_1$ per gallon of solvent) for the paraffinic solvent is 27.72 when compared to that of the benzene solvent of 24.20. Therefore, the resultant reduction of solvent circulation by 47% is not only surprising but also highly desirable because the lower selectivity can be compensated for by simply adding additional stages within the column, whereas the higher circulation rate involves greater capital investment for a larger diameter column and additional, ongoing operating costs.

FIG. 1 illustrates the simplest form of the Extractive-Flashing configuration for the rejection of nitrogen from a lean natural gas stream. This arrangement is particularly useful for moderate recovery of methane as methane-rich gas product which meets the minimum heating value specifications for the pipeline. This arrangement may not be adequate for meeting additional specifications of: (a) methane content of the nitrogen product and (b) nitrogen content of the methane product.

A nitrogen-rich gas stream in line 11 of FIG. 1, which may be at any pressure, enters the bottom of extractor column 12 in extractor unit 10 and flows countercurrently to a stream of lean solvent from line 17 which has been stripped by flashing. An overhead stream in line 13 is the nitrogen product. A bottoms stream of rich solvent in line 15 enters at least one flashing stage 20, exemplified by flashing vessel 22, which produces an overhead stream in line 23 which is optionally compressed in compressor 28 to produce methane-rich gas product 29. The bottoms stream from flashing column 22 passes through line 25, solvent pump 26, line 27, and solvent cooler 16 to line 17 and the top of extractor column 12.

In the process arrangement of FIG. 2, the methane-rich gas product meets the minimum nitrogen content of the pipeline specification. This is accomplished by recycling excess quantities of nitrogen extracted with the rich solvent at the base of the extractor column while improving methane recovery. The nitrogen-rich flash vapors from the intermediate flash stage are also compressed and recycled to the bottom of the extractor column. The methane-rich gas product leaves the overhead of the final flashing stage.

In FIG. 2, a nitrogen-rich gas stream at any pressure is fed by line 31 to extractor column 32 of extractor unit 30 at any pressure and flows countercurrently to a stream of lean solvent, which has been stripped by flashing, entering the top of column 32 through line 39. A nitrogen product leaves through line 33 as the overhead stream, and a bottoms stream of rich solvent passes through line 35 to intermediate flash unit 40 of multiple flashing stages. Entering the flash vessel 42, the rich solvent is separated into (a) an overhead stream of recycled gases in line 43 which is compressed in recycle compressor 46 and returned to extractor column 32 in line 37 and (b) a bottom stream of partially stripped solvent in line 45 which is fed to flash vessel 52 of final flash unit 50, wherein it is separated into an overhead stream 53 which is optionally compressed in compressor 58 and removed through line 59 as methane-rich gas product. A bottoms stream from flash tank 52 passes through line 55, solvent pump 56, line 57, solvent cooler 38, and line 39 to enter the top of extractor column 32.

If the inlet gas contains significant amounts of heavier hydrocarbons (C5+), the equipment configuration of FIG. 3 may be effectively utilized to recover methane-rich gas product under high recovery levels. In this arrangement, the extraction column consists of two extraction sections. The rich solvent is flashed in at least one flashing stage. The vapor leaving the final flashing stage meets the Btu specification of the pipeline. This configuration provides higher recovery of contained methane from a heavier hydrocrbon composition gas stream.

FIG. 3 schematically describes a process for contacting a nitrogen-rich gas at any pressure which enters extractor column 62 of extractor unit 60 through line 61. Column 62 has a primary extractor zone 64 and a secondary extractor zone 66. The gas flows countercurrently to a main stream of stripped solvent from line 67 and to a stream of lean-and-dry solvent from line 69 which has been regenerated. An overhead stream leaves the column in line 63 as the nitrogen product. A bottoms stream of rich solvent passes through line 65 to at least one stage of multiple flashing stages 70 and enters flashing column 72, from which an overhead stream in line 73 is optionally compressed by compressor 74 and leaves the process through line 74a as methane-rich gas product. A bottoms stream of stripped solvent passes through line 75, main solvent pump 76 and line 77 and is then split into a main solvent stream in line 77a and a slipstream in line 79.

The main solvent stream is cooled in solvent cooler 78 and is fed to the midsection of column 62 through line 67. The slipstream passes through line 79, cross exchanger 87, and line 81 to be fed to the midsection of a column 82 of slipstream regenerator unit 80. Column 82 is provided with a reboiler 86 and a reflux apparatus. Overhead passes through line 83, is condensed in condenser 84, and passes through line 93 to accumulator 94 from which the gases are removed through line 98 to join the flash gases in line 74a and become the methane-rich gas product in line 99. A reflux stream in line 95 passes through pump 96 and line 97 to enter the top of column 82. The regenerated solvent, which is lean and dry, passes through line 85, cross exchanger 87, line 88, solvent pump 89, line 91, and solvent cooler 92 to enter line 69 and the top of column 62.

Figure 4:
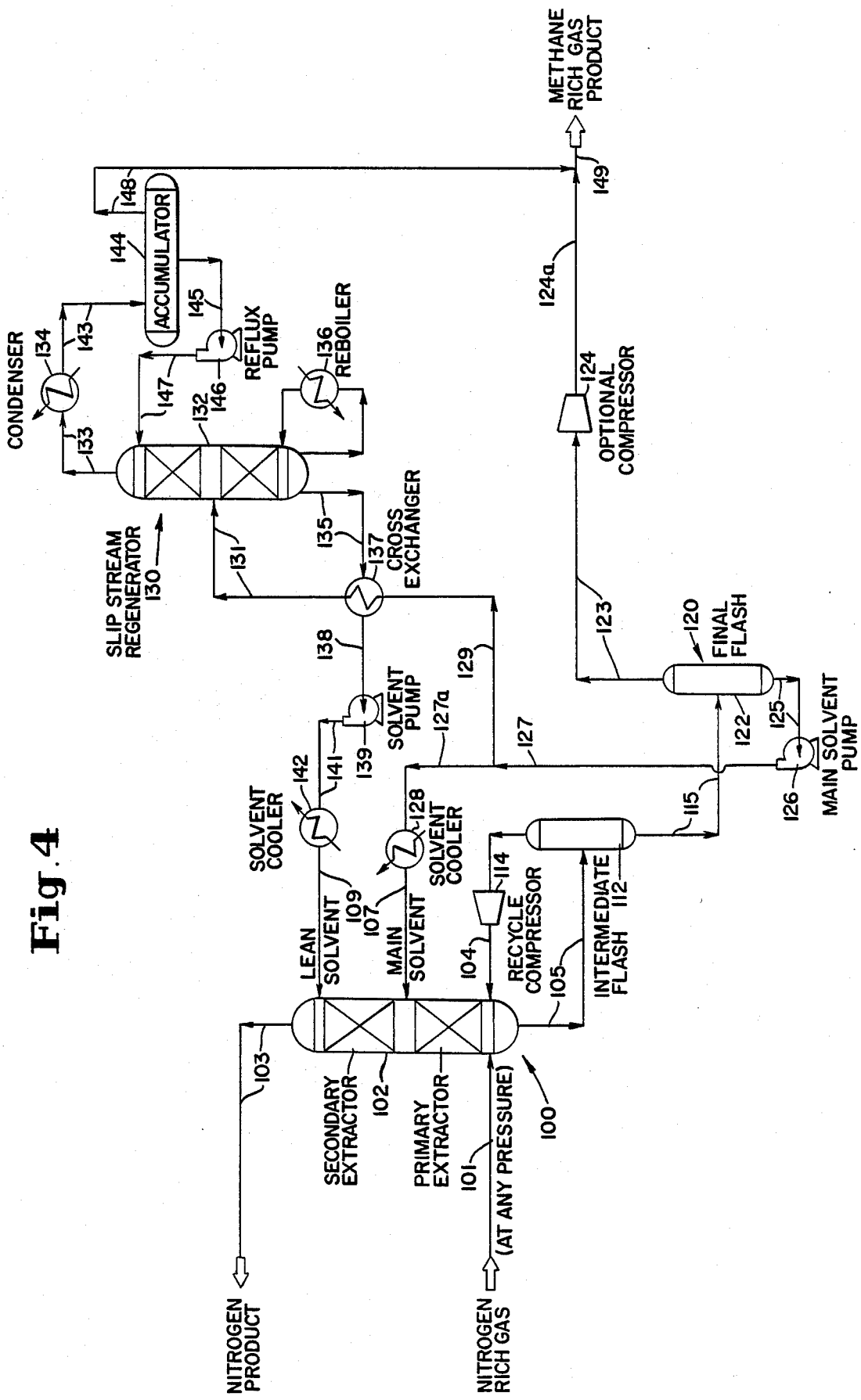
FIG. 4 is a schematic flow sheet, similar to FIG. 3, except that two flashing stages are used.

The FIG. 4 arrangement is quite similar to the apparatus arrangement in FIG. 3. However, the rich solvent is flashed to an interstage pressure level to reject excessive quantities of extracted nitrogen for recycle to the base of the extractor column. This arrangement additionally provides the capability of meeting the nitrogen content specification of the methane-rich gas product. The inlet gas can be at any available pressure.

FIG. 4 shows how nitrogen-rich gas in line 101 at any pressure is fed to the bottom of column 102 of extractor unit 100. Column 102 includes a primary extractor zone and a secondary extractor zone and is fed with recycled gas at its bottom in line 104, a main solvent stream at its midsection in line 107, and a lean solvent srream of lean-and-dry regenerated solvent in line 109 at its top. An overhead stream leaves the top of the column in line 103 as nitrogen product.

A bottoms stream of rich solvent in line 105 enters an intermediate flash column 112 of intermediate flash unit 110 and is split into: (a) an overhead stream in line 113 which is raised in recycle compressor 114 and fed through line 104 to column 102 and (b) a rich solvent bottoms stream which passes through line 115 to final flash unit 120 where it is fed into column 122. It is therein separated into an overhead stream of methane-rich gas in line 123, which is optionally compressed in compressor 124 and fed to line 124a, and a bottoms stream which passes through line 125 and main solvent pump 126 and line 127 before being split into a main solvent stream in line 127a and a slipstream in line 129.

The main solvent stream is cooled by solvent cooler 128 and fed through line 107 to the midsection of extractor column 102. The slipstream in line 129 passes through cross exchanger 137 and feed line 131 to a regenerator column 132 of slipstream regenerator unit 130. Column 132 is equiped with a reboiler 136 and a reflux apparatus. The overhead stream from column 132 leaves through line 133, passes through condenser 134 and line 143 and is stored in accumulator 144. Gases therefrom leave through line 148 to join the flashed gases in line 124a and become a methane-rich gas product in line 149. A reflux stream in line 145 is moved by pump 146 through line 147 to the top of column 132. The regenerated solvent, as the bottoms stream of column 132, leaves through line 135, passes through cross exchanger 137 and line 138, is pumped by solvent pump 139 through line 141 and solvent cooler 142 to enter column 102 through pipeline 109.

Hydrogen Purification

There are many hydrogen-containing off-gases which have methane and other heavier hydrocarbons as diluents. These off-gases vary from 5 mol % to 90 mol % H2. Table III summarizes the performance of various physical solvents for the hydrogen-methane system at 300 psia and −30° F. The inlet gas composition is 65 mol% H2 and 35 mol% Cl. The conditions of pressure, temperature, and composition represent one of the many commercial applications and are selected only for demonstration of this invention. This invention is not to be construed as limited to these conditions.

As indicated in Table IV, the selectivity of the aromatic solvent m-xylene (106 MW) of 21.81 is higher than that of the naphthenic solvent (110 MW) at 19.22 by about 13.5%. The solubility of methane in m-xylene solvent is lower by about 4% than its solubility in the naphthenic solvent. Furthermore, from the earlier teachings of Mehra, one would expect the naphthenic solvent, which has a preferential factor of 17.80, to perform less effectively than the m-xylene solvent which has a preferential factor of 19.42.

However, it was surprisingly determined as shown by the data of Table IV, that to recover the same amount of methane from the inlet gas, about 598 gpm of naphthenic solvent circulation is required when compared to 622 gpm of m-xylene solvent circulation, i.e., a reduction of about 3.8%. This effect is more pronounced for a 110 MW paraffinic solvent.

Figures 5, 6:
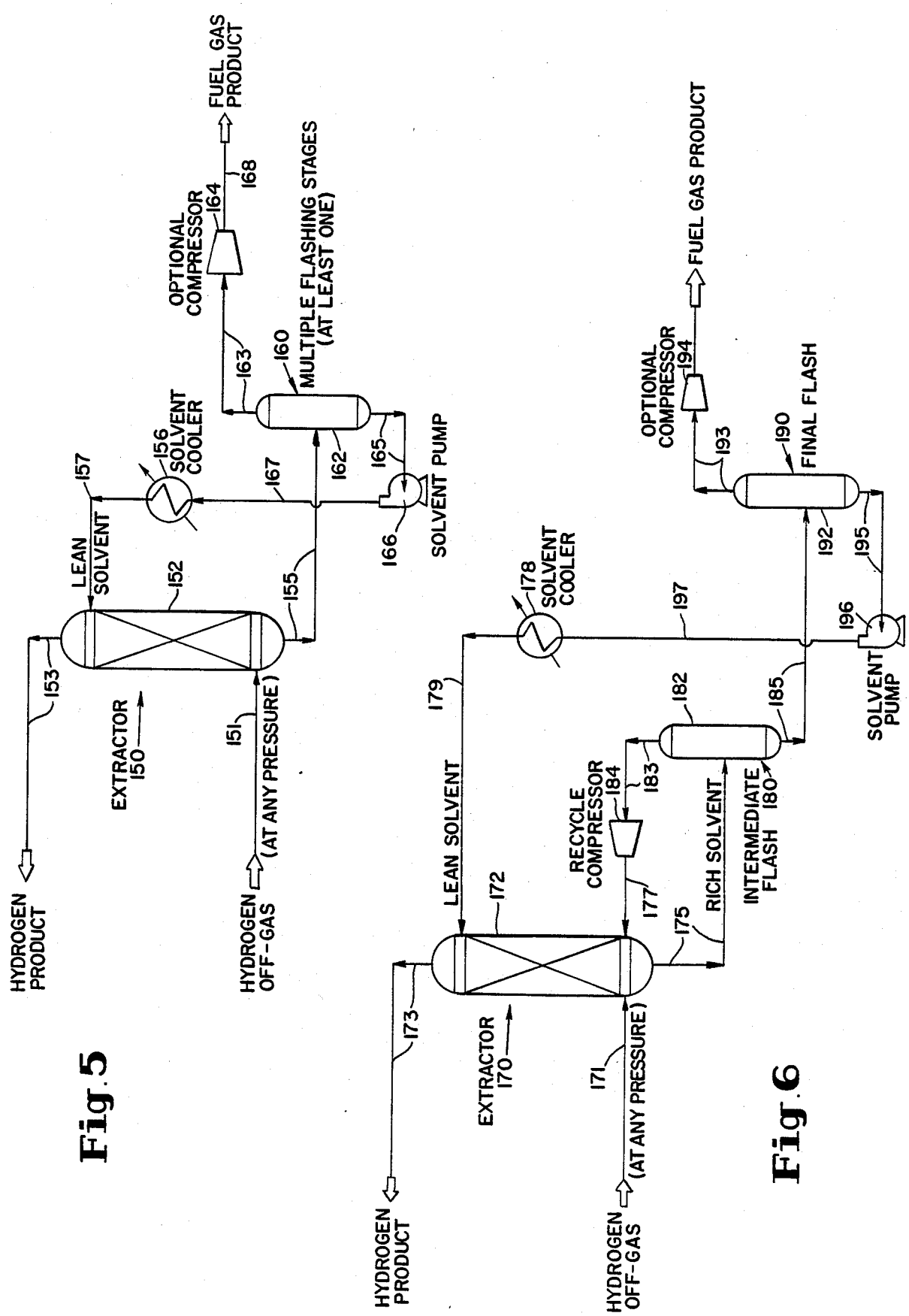
FIG. 5 is a schematic flow sheet for contacting a hydrogen off-gas stream, as from a refinery, at any pressure with a lean solvent stream within an extraction column to produce a hydrogen product as the overhead stream and a rich solvent bottoms stream which is flashed at least once to produce a pure gas product and a stripped solvent stream for recycle to the top of the extractor column.
FIG. 6 is a schematic flow sheet, similar to FIG. 5, except that two flashing stages are used.

FIG. 5 outlines the equipment arrangement that is used for purifying hydrogen to the 95 mol% level with moderate recoveries on the order of 80+%. In this arrangement, the hydrogen-containing off-gas enters the bottom of the extractor column. The rich solvent is flashed in multiple flashing stages consisting of at least one stage.

In FIG. 6, the process equipment arrangement is quite similar to the arrangement of FIG. 5, except that an interstage flashing step is incorporated to improve the recovery of hydrogen to the 90+% level. This is accomplished by selectively separating the excessive quantities of hydrogen in the rich solvent through the interstage flash and recycling after compression to the bottom of the extractor column. The hydrogen product leaves the process unit with minimal plant pressure drop.

The hydrogen off-gas in FIG. 6, which may be under any pressure at which it is available, enters the bottom of an extraction column 172 of a extraction unit 170 through pipeline 171. It is joined by recycled gases in line 177. Both gases then flow countercurrently to a stream of lean solvent entering the top of the column through line 179 after being cooled in solvent cooler 178, thereby producing an overhead stream in line 173 as hydrogen product and a bottoms stream 175 of rich solvent which is flashed in flash column 182 of intermediate flash unit 180 to form overhead gas stream 183 which is recycled through recycle compressor 184 and line 177 to the bottom of column 172. Bottoms stream 185 of stripped solvent flows to flash column 192 of

TABLE IV

PHYSICAL SOLVENT PERFORMANCE
NITROGEN-METHANE SYSTEM

BASIS: 1000 LB-MOL/HR FEED CONTAINING 65% H2 AND 35% C1
25% RECOVERY OF METHANE IN SOLVENT @ 300 PSIA & −30° F.
STP = 14.696 psia @ 60° F.

| TYPE | SOLVENT MW | GAL/MIN STP | C1 SCF/GAL | ALPHA H2/C1 | PREF. FACTOR | S/F RATIO GAL/SCF |
|---|---|---|---|---|---|---|
| Paraffinic | 75 | 374 | 1.48 | 16.86 | 24.96 | 0.0591 |
| Paraffinic | 85 | 416 | 1.33 | 16.28 | 21.63 | 0.0658 |
| Paraffinic | 100 | 486 | 1.14 | 15.84 | 18.03 | 0.0768 |
| Paraffinic | 110 | 532 | 1.04 | 15.40 | 16.02 | 0.0841 |
| Paraffinic | 120 | 577 | 0.96 | 14.99 | 14.38 | 0.0912 |
| Paraffinic | 130 | 621 | 0.89 | 14.51 | 12.93 | 0.0982 |
| Paraffinic | 140 | 666 | 0.83 | 14.21 | 11.82 | 0.1052 |
| Naphthenic | 75 | 449 | 1.23 | 22.80 | 28.12 | 0.0710 |
| Naphthenic | 85 | 493 | 1.12 | 21.74 | 24.42 | 0.0779 |
| Naphthenic | 110 | 598 | 0.93 | 19.22 | 17.80 | 0.0945 |
| Naphthenic | 130 | 701 | 0.79 | 18.78 | 14.82 | 0.1109 |
| Benzene | 78 | 653 | 0.85 | 22.16 | 18.78 | 0.1032 |
| Toluene | 92 | 678 | 0.82 | 20.99 | 17.13 | 0.1072 |
| Ethylbenzene | 106 | 614 | 0.90 | 21.75 | 19.60 | 0.0971 |
| m-Xylene | 106 | 622 | 0.89 | 21.81 | 19.42 | 0.0983 |
| Mesitylene | 120 | 703 | 0.79 | 20.75 | 16.36 | 0.1111 |

The overhead from the final flashing stage is rejected to the fuel system and may be compressed if so desired. The flashed solvent is pumped and cooled for recycle to the extractor column. The hydrogen product is delivered with minimal pressure drop through the Mehra process unit.

FIG. 5 shows a process for treating a hydrogen off-gas in line 151 which enters at any pressure the bottom of an extractor column 152 of extractor unit 150. Column 152 is fed with stripped lean solvent line 157 at its top. An overhead stream passes through line 153 and leaves the process as hydrogen product. A bottoms stream of rich solvent passes through line 155 to flash column 162 of multiple flashing stages 160. It is therein split into an overhead stream in line 163 and a bottoms stream in line 165. The overhead stream is optionally compressed by compressor 164 and leaves the process as fuel gas product in line 168. The bottoms stream in line 165 is pumped by solvent pump 166 through line 167 and solvent cooler 156 into pipeline 157 and column 152.

final flash unit 190, producing an overhead gas stream 193 which is optionally compressed in compressor 194 to form methane-rich gas product stream 198. Bottoms stream 195 from column 192 flows through line 195, solvent pump 196, and line 197 to enter solvent cooler 178.

Figure 7:
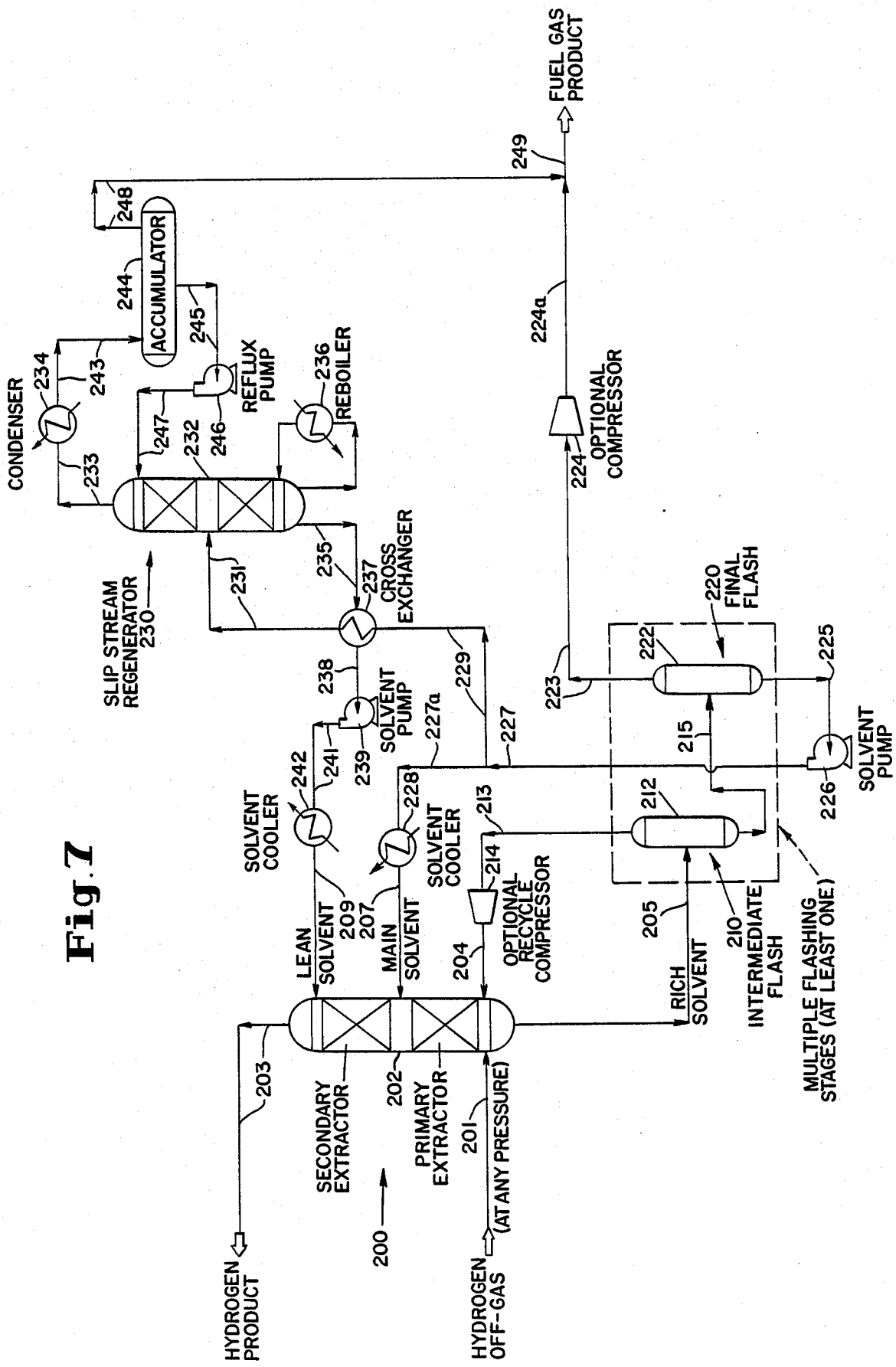
FIG. 7 is another schematic flow sheet, similar to FIG. 4, for contacting a hydrogen off-gas stream at any pressure with a main stream of stripped solvent and a cleanup stream of lean solvent.

In order to further improve the purity of the hydrogen product to 99+mol% under high recovery levels on the order of 95+%, the equipment arrangement shown in FIG. 7 may be effectively utilized. This process arrangement uses the slipstream concept in conjunction with the flashing arrangement of FIG. 6. The main solvent stream aids in the bulk removal of methane and heavier components, and the lean solvent, regenerated from the slip solvent stream, provides the final polishing to the desired purity on the order of 99 mol% H2.

FIG. 7 schematically shows the treatment of a hydrogen off-gas stream in line 201 at any pressure within extractor column 202 of extractor unit 200. Column 202 has a primary extractor zone and a secondary extractor zone and receives recycled gases through line 204 at its bottom, a main solvent stream of stripped solvent through line 207 at its midsection, and a regenerated solvent stream of lean-and-dry solvent in pipeline 209 at its top. An overhead stream of hydrogen product leaves through line 203.

A bottoms stream of rich solvent leaves through line 205 and is fed to column 212 of intermediate flash unit 210. Within column 212, it is split into an overhead stream 213 of flashed gases which are recycled through recycle compressor 214 to the bottom of column 202 and a bottoms stream of partially stripped solvent in line 215.

Stream 215 is fed to flash column 222 of final flash unit 220. It is therein separated into a stream of flashed gases which passes through line 223, compressor 224, and line 224a. The stripped solvent passes through line 225, solvent pump 226, and line 227 before being split into a main solvent stream in line 227a and a slipstream in line 229. The main solvent stream is cooled in solvent cooler 228 and enters the midsection of column 202 through line 207.

The slipstream passes through line 229, cross exchange 237, and line 231 to enter the midsection of slipstream regenerator column 232 of slipstream regenerator unit 230. Column 232 has a reboiler 236 and a reflux apparatus. An overhead stream of gases in line 233 is condensed in condensor 234 and passes through line 243 to accumulator 244 from which gases move through line 248 to join the flashed gases in line 224a to form the fuel gas product in line 249. Reflux from accumulator 244 moves through line 245, pump 246, and line 247 to return to the top of column 232. The bottoms stream of lean-and-dry solvent, which has been regenerated, passes through line 235, cross exchanger 237, line 238, solvent pump 239, line 241, and solvent cooler 242 into line 209 and the top of column 202.

Olefin Extraction

There are several gas streams that contain desirable olefins, such as ethylene and propylene, along with methane and hydrogen. To demonstrate applications of physical solvents, the performance data for the methane-ethylene system at 200 psia and +10° F. from a very lean stream containing 95 mol% C1 and 5 mol% C2= are summarized in Table V. These conditions of pressure, temperature, and composition represent one of the many commercial applications and are selected only for demonstration of this invention.

This invention is not to be construed as limited to these conditions.

In comparing the selectivity data for benzene solvent with that of 75 MW paraffinic solvent, it is clear that the paraffinic solvent is less attractive because it has a selectivity, defined as $KC1/KC2$=alpha, of 4.89 versus 6.93 for the benzene solvent. Based on the comparison of preferential factors for benzene and 75 MW paraffinic solvent, one would expect that the paraffinic solvent would be less effective. However, to recover 25% of contained ethylene from such a lean stream under low pressure of 200 psia at a temperature of +10° F., the paraffinic solvent requires only 141 gpm circulation as compared to 168 gpm for the benzene solvent, i.e., a surprising reduction of about 16%.

Figure 8:
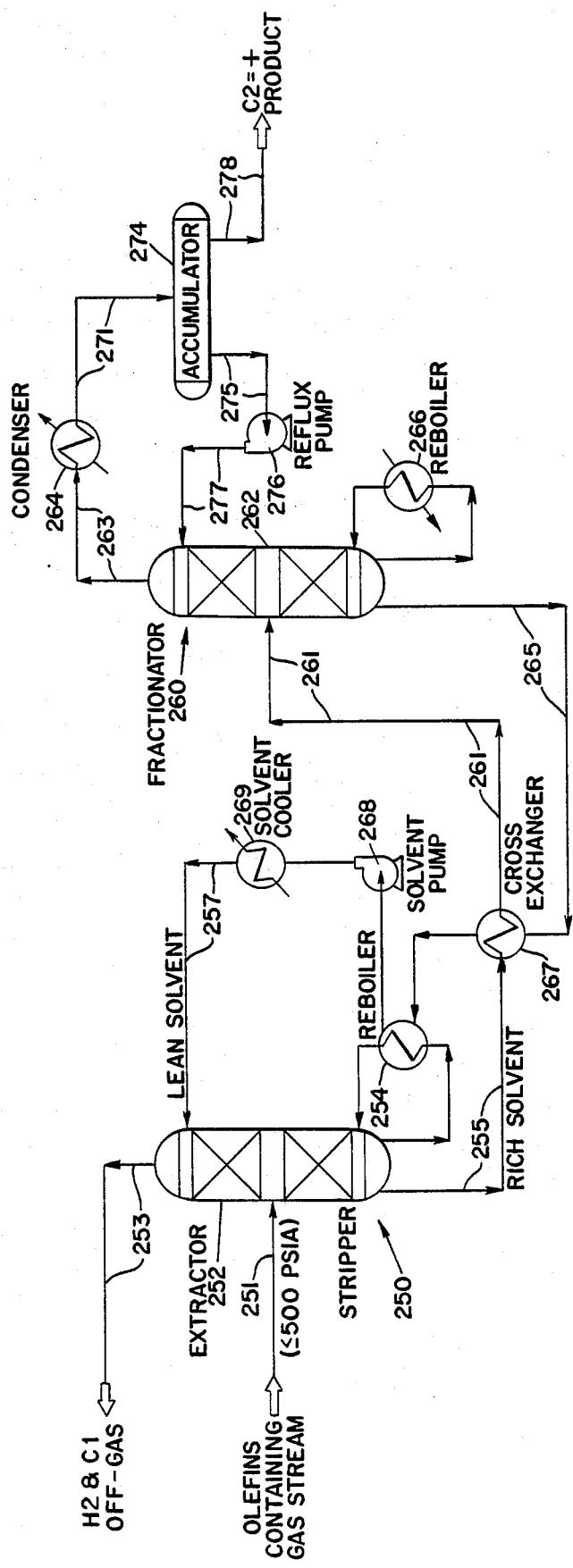
FIG. 8 is a schematic flow sheet for extractive stripping of a olefins-containing gas stream, at a pressure of at least 500 psia, in an extractor/stripper column with a lean solvent fed to the top thereof to produce a mixture of hydrogen and methane as the off-gas overhead stream and a rich solvent bottoms stream from which ethylene-plus gases are recovered as product.

The Extractive-Stripping arrangement of the Mehra Process for olefin extraction operating under 500 psia is shown in FIG. 8. The rich solvent at the bottom of the extractor-stripper column is capable of meeting a stringent methane specification for the ethylene product. The extracted C2= +hydrocarbons are separated from the solvent in the fractionator. The fractionator is refluxed to minimize solvent losses. In this arrangement, the methane and hydrogen leave the top of the extractor-stripper column with minimal overall pressure drop.

FIG. 8 shows a process for contacting an olefins-containing gas stream at no more than 500 psia with regenerated solvent to produce an off-gas stream of hydrogen and methane and an ethylene-plus product stream. The olefins-containing stream in line 251 enters the midsection of extractor stripper column 252 of unit 250 which is equiped with a reboiler 254 and therein flows countercurrently to a stream of lean solvent from line 257. An overhead stream in pipeline 253 leaves the process as a mixture of hydrogen and methane off-gas. A rich solvent, as the bottoms stream, passes through line 255 through cross exchanger 267 and pipeline 261 to enter the midsection of fractionator column 262 of a fractionator unit 260.

Column 262 has a reboiler 266 and a reflux apparatus. Overhead gases pass through line 263, condenser 264, and line 271 to enter accumulator 274 from which ethylene-plus product is withdrawn through line 278. Reflux passes through line 275, reflux pump 276, and line 277 to enter the top of column 262. The bottoms stream of lean-and-dry regenerated solvent passes through line 265, cross exchanger 267, reboiler 254, solvent pump 268, solvent cooler 269, and pipeline 257 to enter the top of column 252.

TABLE V
PHYSICAL SOLVENT PERFORMANCE
METHANE-ETHYLENE SYSTEM

BASIS: 1000 LB-MOL/HR FEED CONTAINING 95% C1 AND 5% C2=
25% RECOVERY OF ETHYLENE IN SOLVENT @ 200 PSIA & +10° F.
STP = 14.696 psia @ 60° F.

| TYPE | SOLVENT MW | GAL/MIN STP | C2= SCF/GAL | ALPHA C1/C2= | PREF. FACTOR | S/F RATIO GAL/SCF |
|---|---|---|---|---|---|---|
| Paraffinic | 75 | 141 | 0.56 | 4.89 | 2.75 | 0.0222 |
| Paraffinic | 100 | 180 | 0.44 | 4.86 | 2.13 | 0.0284 |
| Paraffinic | 110 | 198 | 0.40 | 4.83 | 1.93 | 0.0313 |
| Paraffinic | 140 | 255 | 0.31 | 4.71 | 1.46 | 0.0403 |
| Naphthenic | 75 | 144 | 0.55 | 5.66 | 3.10 | 0.0228 |
| Naphthenic | 110 | 202 | 0.39 | 5.39 | 2.11 | 0.0319 |
| Naphthenic | 130 | 239 | 0.33 | 5.36 | 1.77 | 0.0378 |
| Benzene | 78 | 168 | 0.47 | 6.93 | 3.26 | 0.0266 |
| Toluene | 92 | 182 | 0.43 | 6.73 | 2.92 | 0.0288 |
| Ethylbenzene | 106 | 197 | 0.40 | 5.71 | 2.29 | 0.0311 |
| m-Xylene | 106 | 199 | 0.04 | 5.72 | 2.27 | 0.0314 |
| Mesitylene | 120 | 228 | 0.35 | 5.63 | 1.95 | 0.0361 |

Figure 9:
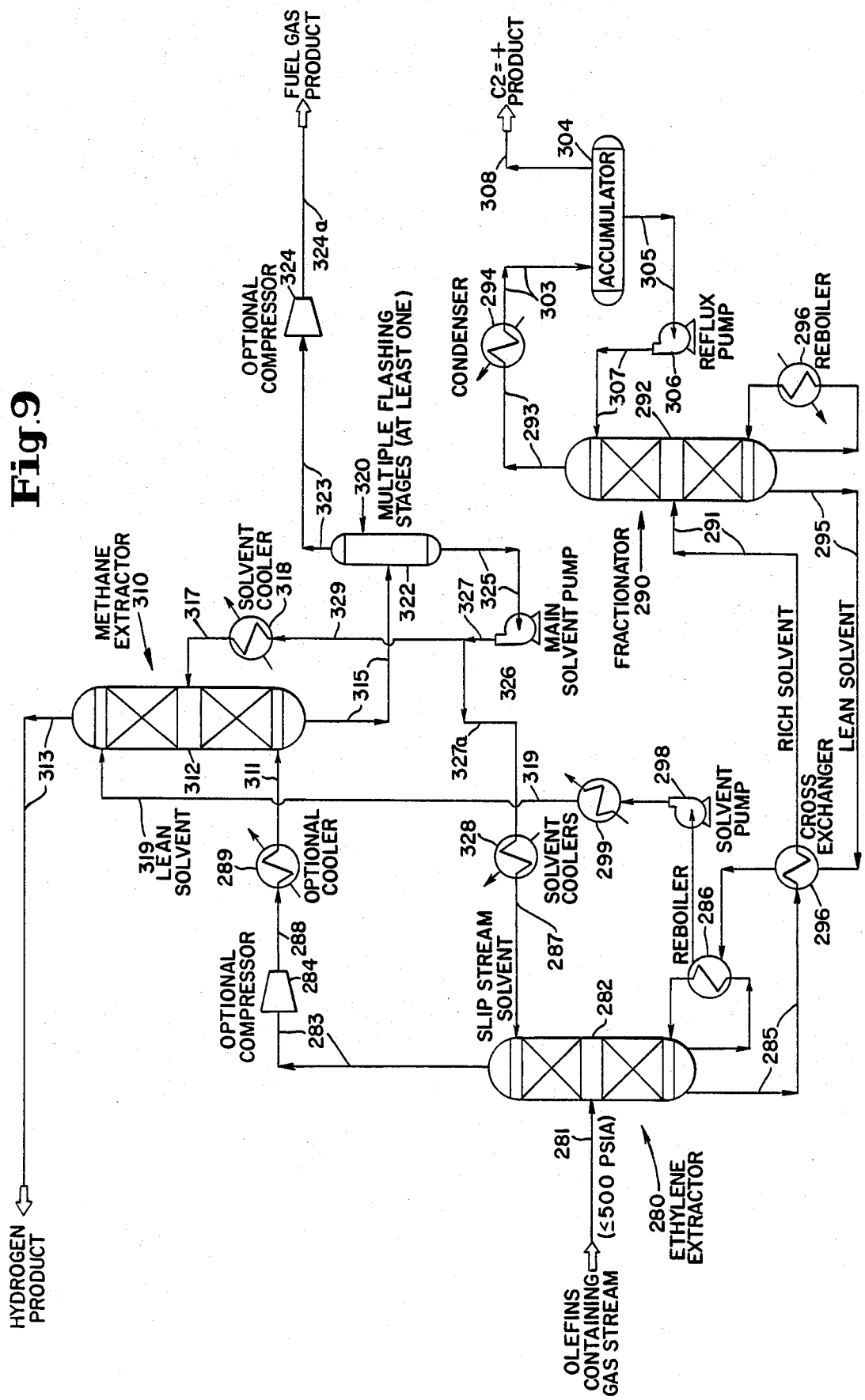
FIG. 9 is a schematic flow sheet which is similar to FIG. 8 except that the overhead mixture of hydrogen and methane is fed to the bottom of a methane extractor to produce a hydrogen product as the overhead stream.

If it is desired to additionally separate the methane from hydrogen, the equipment arrangement of FIG. 9 can be utilized. In this arrangement, a single solvent system is utilized for producing hydrogen, fuel gas and C2=+products. Next, methane is extracted from the gas to produce a hydrogen product. The ethylene extractor overhead may be compressed, if economically desirable, prior to methane extraction. However, methane can be extracted from hydrogen at the available pressure to any purity and recovery level. Even though the methane extractor system shown is slightly different from FIGS. 5, 6 and 7, any combination of process features such as a power recovery turbine or intermediate flashing and recompression, may be used.

FIG. 9 illustrates a process for obtaining a hydrogen product, a fuel gas product, and an ethylene-plus product from an olefins-containing gas stream at at least 500 psia by extraction with a physical solvent. The olefins-containing gas stream in pipeline 281 enters the midsection of a column 282 of ethylene extractor unit 280. Column 282 has a reboiler 286 and receives at its top a slipstream of regenerated solvent through line 287. An overhead stream of gases passes through line 283, compressor 284, line 288, cooler 289, and line 311 to enter the bottom of a methane extractor column 312 of methane extractor unit 310. Column 312 has a primary extractor zone and a secondary extractor zone. Column 312 receives a stream of stripped solvent through line 317 at its midsection and a stream of regenerated solvent at its top through line 319. An overhead stream leaves through pipeline 313 as hydrogen product, and a bottoms stream of rich solvent leaves through line 315 to enter flash column 322 of multiple flash stages 320.

Flashed gases pass through line 323, compressor 324, and line 324a as fuel gas product. The stripped solvent passes through line 325, pump 326, and line 327 before being split into a main solvent stream in line 327a and a slipstream in line 329 which passes through solvent cooler 319 and line 317 to enter column 312. The main solvent stream of line 327a is cooled in solvent cooler 328 and enters the top of column 282 through line 287.

The rich solvent bottoms stream of column 282 passes through line 285, cross exchanger 296, and line 291 to enter the midsection of column 292 of fractionator unit 290. Column 292 has a reboiler 296 and a reflux apparatus. Overhead gases pass through line 293, condenser 294, and line 303 to enter accumulator 304 from which ethylene-plus gases leave as product through line 308. Reflux passes through line 305, reflux pump 306, and line 307 to enter the top of column 292. A bottoms stream from column 292 passes through line 295, cross exchanger 296, reboiler 286, solvent pump 298, and solvent cooler 299 to enter the top of column 312 through line 319.

The continuous process of this invention for separating components of a hydrocarbon gas stream, which are selected from the group consisting of hydrogen, nitrogen, methane, ethylene, ethane, higher saturated and unsaturated hydrocarbons, and mixtures thereof, comprises the following steps:

A. countercurrently contacting the hydrocarbon gas stream with a physical solvent selected from the group consisting of:
(1) paraffinic solvents having molecular weights ranging from 75 to 140 and UOP characterization factors ranging from 12.0 to 13.5, the factors being independent of the aromatic content of the paraffinic solvents,
(2) naphthenic solvents having molecular weights ranging from 75 to 130 and UOP characterization factors ranging from 10.5 to 12.0, these factors being independent of the aromatic content of the naphthenic solvents, and
(3) benzene and toluene, to produce an overhead stream which is at least rich in at least one of the components and a rich solvent bottoms stream; and B. recovering the lean physical solvent from the rich solvent bottoms stream and recycling the recovered stream to the contacting of Step A.

As a general rule for all embodiments of this invention, when a stripping section is utilized in a column, it is important to avoid operating near the system critical preesure as evidenced by the difference between liquid and vapor density being less than 20 pounds per cubic foot.

Because it will be readily apparent to those skilled in the art of treating hydrocarbon gases containing components needing to be separated and recovered that innumerable variations, modifications, applications, and extensions of the examples and principles hereinbefore set forth can be made without departing from the spirit and the scope of the invention, what is hereby defined as such scope and is desired to be protected should be measured, and the invention should be limited, only by the following claims.

What is claimed is:

1. A continuous process for separating components of a hydrocarbon gas feed stream, said components being selected from the group consisting of hydrogen, nitrogen, methane, ethylene, ethane, heavier saturated and unsaturated hydrocarbons, and mixtures thereof by the following steps:
   A. counter-currently contacting said hydrocarbon gas stream with a physical solvent selected from the group consisting of:
   (1) paraffinic solvent having molecular weights ranging from 75 to 140 and UOP characterization factors ranging from 12.0 to 13.5, said factors being independent of the aromatic content of said paraffinic solvents,
   (2) naphthenic solvents having molecular weights ranging form 75 to 130 and UOP characterization factors ranging from 10.5 to 12.0, said factors being independent of the aromatic content of said naphthenic solvents, and
   (3) benzene and toluene, to produce an overhead stream which is rich in one of said components and a rich solvent bottoms stream which is rich in at lesst one of another of said components and;
   B. flashing said rich solvent bottoms stream to obtain said lean physical solvent and recycling the recovered solvent stream to the contacting of Step A.

2. The continuous process of claim 1 wherein
   (1) the gas feed to countercurrent contacting of step A contains at least hydrogen and methane and produces an overhead stream of hydrogen product;
   (2) said flashed solvent stream additionally countercurrently contacts a hydrocarbon gas stream containing at least hydrogen, methane, ethylene and ethane to produce the said gas feed of step (1) as an overhead stream and an ethylene rich solvent bottoms stream; and
   (3) regenerating said ethylene rich solvent stream to produce an ethylene plus product as an overhead product and a lean regenerated solvent stream for recycling to countercurrent contact of Step A in step 1 of this claim.

3. The process of claim 1, wherein said flashing produces an overhead stream which is rich in said at least another of said components.

4. The process of claim 3, wherein said contacting produces a gas product stream of hydrogen and/or nitrogen and a solvent bottoms stream rich in $C_1+$ components.

5. The process of claim 4, wherein said bottoms solvent stream is flashed to produce a fuel gas product and a bottom stream of stripped solvent.

6. The process of claim 5, wherein said stripped solvent stream is split into a main solvent stream which is fed to said contacting of said Step A and a slipstream which is fed to a second contacting step or to a regenerastion step.

7. The continuous process of claim 1, wherein:
A. said hydrocarbon gas feed stream is a nitrogen-rich natural gas stream containing more than 3 mol % nitrogen as one said component to be separated; and
B. a nitrogen product stream is separated as said overhead stream.

8. The improved process of claim 7 wherein said recovered solvent stream is split into:
(1) a main solvent stream which is fed to said contacting of step A; and
(2) a slip stream which is fed to a regenerator column.

9. The improved process of claim 7, wherein:
A. said flashing is conducted in at least two stages; and
B. the flashed gases from the first stage of said at least two stages are compressed and recycled to said contacting of said step A.

10. The improved process of claim 9. wherein the last stage of said at least two stages produces an overhead product stream and a bottoms stream of stripped solvent which is recycled to said contacting of said step A.

11. The improved process of claim 10, wherein said stripped solvent stream is split into:
(1) a main solvent stream which is fed to said contacting of step A; and
(2) a slipstream which is fed to a regenerator column.

12. The improved process of claim 11 or 8, wherein said regenerator column produces an overhead stream which is partially condensed to produce a gas product stream and a reflux stream which is returned to the top of said regenerator column.

13. The improved process of claim 12, wherein said regenerator column produces a bottoms stream of lean regenerated solvent which is fed to the counter-current contacting of step A.

14. The continuous process of claim 1, wherein said overhead stream is a hydrogen product.

15. The improved process of claim 14 wherein said recovered solvent stream is split into:
(1) a main solvent stream which is fed to said contacting of step A; and
(2) a slip stream which is fed to a regenerator column.

16. The improved process of claim 14 wherein:
A. said flashing is conducted in at least two stages; and
B. the flashed gases from the first stage of said at least two stages are compressed and recycled to said contacting of said step A.

17. The improved porcess of claim 16 wherein the last stage of the flashing stages produces a gas product stream and a bottoms stream of stripped solvent which is recycled to said contactingof said step A.

18. The improved process of claim 17, wherein said bottoms stripped solvent stream is split into:
(1) a main solvent stream which is fed to said contacting of step A; and
(2) a slipstream whichis fed to a regenerator column.

19. The improved process of claim 18 or 15, wherein said regenerator column produces an overhead stream which is partially condensed to produce an overhead gas product stream and a reflux stream which is returned to the top of said regenerator column.

20. The improved process of claim 19, wherein said regenerator column produces a bottoms stream of lean regenerated solvent which is fed to the counter-current contacting of step A.

* * * * *